United States Patent
Chen et al.

(10) Patent No.: US 12,162,843 B2
(45) Date of Patent: Dec. 10, 2024

(54) HIGH-PURITY THERMOSTABLE CRYSTAL FORM OF SUBSTITUTED 3-ISOXAZOLIDINONE COMPOUND, PREPARATION METHOD THEREFOR AND APPLICATION THEREOF

(71) Applicant: ZHEJIANG ZHUJI UNITED CHEMICALS CO., LTD., Zhejiang (CN)

(72) Inventors: Bangchi Chen, Zhejiang (CN); Baochuan Guan, Zhejiang (CN); Qiuju Sheng, Zhejiang (CN); Hongwei Zhang, Zhejiang (CN); Xianbo Xu, Zhejiang (CN); Yonglin Zhang, Zhejiang (CN); Xiaoyan Xu, Zhejiang (CN); Haiping Mu, Zhejiang (CN); Zhuoya Zhang, Zhejiang (CN)

(73) Assignee: ZHEJIANG ZHUJI UNITED CHEMICALS CO., LTD., Shaoxing (CN)

( * ) Notice: Subject to any disclaimer, the term of this patent is extended or adjusted under 35 U.S.C. 154(b) by 547 days.

(21) Appl. No.: 17/525,170

(22) Filed: Nov. 12, 2021

(65) Prior Publication Data
US 2022/0089553 A1 Mar. 24, 2022

Related U.S. Application Data

(63) Continuation of application No. PCT/CN2019/086559, filed on May 13, 2019.

(51) Int. Cl.
*C07D 261/04* (2006.01)
*A01N 43/80* (2006.01)

(52) U.S. Cl.
CPC .......... *C07D 261/04* (2013.01); *A01N 43/80* (2013.01); *C07B 2200/13* (2013.01)

(58) Field of Classification Search
CPC .... C07D 261/04; A01N 43/80; C07B 2200/13
See application file for complete search history.

(56) References Cited

U.S. PATENT DOCUMENTS 4,405,357 A   9/1983   Chang

FOREIGN PATENT DOCUMENTS

| CN | 103458691 A | 12/2013 |
| CN | 106455569 A | 2/2017 |
| CN | 109068631 A | 12/2018 |
| CN | 109776442 A | 5/2019 |
| WO | 2012148689 A2 | 11/2012 |
| WO | 2017025418 A1 | 2/2017 |
| WO | 2019030177 A1 | 2/2019 |

*Primary Examiner* — Zohreh A Fay (57) ABSTRACT

The application provides a high-purity thermostable crystal form of a substituted 3-isoxazolidinone compound, a preparation method therefor and an application thereof. The High-purity thermostable crystal form is prepared by a particular method of the present technology and is determined by single-crystal X-ray diffraction as an orthorhombic crystal, featuring a space group of P212121 and lattice parameters of a=9.2301(2) Å, b=11.0751(3) Å, c=12.7554(3) Å, $\alpha=90°$, $\beta=90°$, and $\gamma=90°$. The orthorhombic crystal can be conveniently applied in preparation of agrochemical formulations, such as a suspension concentrate and a water dispersible granule, and the new formulations prepared have a better herbicidal activity and crop safety.

12 Claims, 3 Drawing Sheets

HIGH-PURITY THERMOSTABLE CRYSTAL FORM OF SUBSTITUTED 3-ISOXAZOLIDINONE COMPOUND, PREPARATION METHOD THEREFOR AND APPLICATION THEREOF

CROSS-REFERENCE TO RELATED APPLICATIONS

This application is a continuation of International Patent Application No. PCT/CN2019/086559, filed on May 13, 2019. The content of the aforementioned application, including any intervening amendments thereto, is incorporated herein by reference in its entirety.

TECHNICAL FIELD

This application relates to agrochemical field, and more particularly to a high-purity thermostable crystal form of 2-[(2,4-dichlorophenyl)methyl]-4,4-dimethyl-3-isoxazolidinone compound, preparation method therefor and application thereof.

BACKGROUND

2-[(2,4-Dichlorophenyl)methyl]-4,4-dimethyl-3-isoxazolidinone is a new promising compound in the family of isoxazolinone herbicides. It has been brought to the forefront of many companies in recent years due to its low volatility, compared with Clomazone which is prevailing in the herbicide market presently.

Clomazone (Formula II) is presented with the chemical name of 2-(2-chlorophenyl)methyl-4,4-dimethyl-3-isoxazolidinone and by the following structural formula:

II

BCPC reported Compound II as an oily substance at room temperature, with a melting point of 25.0° C.-34.7° C. and a boiling point of 275.4° C.-281.7° C.

Compared to Clomazone (Formula II), the 2-[(2,4-dichlorophenyl)methyl]-4,4-dimethyl-3-isoxazolidinone compound (Formula I) has a chlorine atom that substitutes for the hydrogen atom at Position 4 on the benzene ring, shown by the following structural formula:

I

FMC Corporation reported the 2-[(2,4-dichlorophenyl)methyl]-4,4-dimethyl-3-isoxazolidinone compound (Formula I) as an oily substance at room temperature (Embodiment 22, U.S. Pat. No. 4,405,357).

FMC Corporation disclosed the 2-[(2,4-dichlorophenyl)methyl]-4,4-dimethyl-3-isoxazolidinone compound (Formula I) used as a selective pre-emergence herbicide for weed control in corn, rice, sorghum, barley, rye, rape (Patent WO2012148689). The patent also reported a method for preparing a single-dose suspension concentrate (SC) formulation of the 2-[(2,4-dichlorophenyl)methyl]-4,4-dimethyl-3-isoxazolidinone compound (Formula I), by taking an oily substance prepared by the method of U.S. Pat. No. 4,405,357 as an active ingredient and pulverizing the active ingredient in an intermediate procedure. However, how to pulverize the oily substance is not specifically disclosed. As for pulverizing, the present technology is to first adsorb an oily active ingredient on a solid carrier (such as white carbon black), mix the active ingredient into a master powder, and then mechanically pulverize the master powder. In addition to increasing the formulation cost as a result of the use of additional additives and processing equipment, the present technology also poses a major safety and environmental hazard, because a large amount of dust is generated during mechanical pulverizing. Furthermore, the formulation produced thereby is often of unstable quality.

In 2016, Bayer filed a patent for a new application of the 2-[(2,4-dichlorophenyl)methyl]-4,4-dimethyl-3-isoxazolidinone compound (Formula I) as a foliar (post-emergence) herbicide (WO2017025418). However, the type of formulation thereof and its preparation method were not disclosed.

In 2018, Bayer disclosed a method for preparing a SC formulation of active agrochemical ingredient (a) whose melting point ranges from 50° C. to 80° C. mixed with the 2-[(2,4-dichlorophenyl)methyl]-4,4-dimethyl-3-isoxazolidinone compound (Formula I) (CN109068631A). The method comprises melting the agrochemical ingredient (a), adding the melted agrochemical ingredient (a) together with the 2-[(2,4-dichlorophenyl)methyl]-4,4-dimethyl-3-isoxazolidinone compound (Formula I) to water containing at least an ionic dispersant and/or a nonionic dispersant and a carrier material while stirring, then cooling to below the melting point of the active component (a), and grinding.

Recently, Maxunitech Inc. disclosed a specific method for preparing a monoclinic crystal of the 2-[(2,4-dichlorophenyl)methyl]-4,4-dimethyl-3-isoxazolidinone compound (Formula I) with a melting point of 45° C. (CN201910188658.2). The monoclinic crystal features a space group of P21/C and lattice parameters of a=10.6368 (2) Å, b=11.8019 (3) Å, c=20.0931 (4), α=90°, β=92.825° (1), and γ=90°. However, the monoclinic crystal is not suitable for direct preparation of green and environmentally friendly agrochemical formulations, like a SC formulation. Generally speaking, SC formulation requires active agrochemical ingredient has the melting point greater than 60° C. and solubility in water less than 100 mg/L, and the active agrochemical ingredient remains stable in an aqueous solution (Xu Yan. Pesticide Liquid Formulation, Chemical Industry Press: P31). An active agrochemical ingredient with a melting point lower than 60° C. is prone to melting and softening during pulverizing and grinding processes, affecting its physical stability of the SC formulation, leading to flocculation and paste formation. In addition, such formulated SC is prone to delamination and particle size enlargement during storage, which affects its use.

Currently, the 2-[(2,4-dichlorophenyl)methyl]-4,4-dimethyl-3-isoxazolidinone compound (Formula I) has not been reported as a water dispersible granule (WG) formulation. The use of 2-[(2,4-dichlorophenyl)methyl]-4,4-dimethyl-3- isoxazolidinone compound (Formula I) as an pre-emergence herbicide for weed control in wheat has not been reported neither.

To address the shortcomings of the present technology, the inventors discovered a more thermostable crystal of the 2-[(2,4-dichlorophenyl)methyl]-4,4-dimethyl-3-isoxazolidinone compound (Formula I) through enormous amount of experimental design and laboratory validation. The inventors also discovered this high-purity thermostable crystal can be more conveniently and efficiently used to prepare green and environmentally friendly agrochemical formulations, such as suspension concentrate (SC) or water dispersible granule (WG).

SUMMARY OF THE INVENTION

To address the shortcomings of the present technology, the application provides a high-purity thermostable crystal form of 2-[(2,4-dichlorophenyl)methyl]-4,4-dimethyl-3-isoxazolidinone compound (Formula I), efficient preparation method therefor and application thereof.

An object of the application is to provide a method for preparing a stable seed crystal of the 2-[(2,4-dichlorophenyl)methyl]-4,4-dimethyl-3-isoxazolidinone compound (Formula I), comprising the following steps: The said sub-thermostable monoclinic crystal of the 2-[(2,4-dichlorophenyl)methyl]-4,4-dimethyl-3-isoxazolidinone compound (Formula I) with a melting point of 45° C. is prepared by the method of Patent CN201910188658.2.

The sub-thermostable monoclinic crystal is dissolved in organic solvent A, slowly volatilizing the solvent A through heating, cooling and re-heating, and then crystallizing to obtain an orthorhombic seed crystal of the 2-[(2,4-dichlorophenyl)methyl]-4,4-dimethyl-3-isoxazolidinone compound (Formula I), wherein the solvent A is one or more selected from the group consisting of alkanes and cycloalkanes; the weight ratio of the 2-[(2,4-dichlorophenyl)methyl]-4,4-dimethyl-3-isoxazolidinone compound (Formula I) to the solvent A is 1:10-20; the solvent A is first heated to 40° C.-90° C., cooled to −10° C.-10° C. for 10-20 hours, and re-heated to 15° C.-40° C.; and a volatilization process lasts for 3 to 30 days. Preferably, the solvent A is petroleum ether, wherein a boiling range of petroleum ether is 60° C. and 90° C.; the weight ratio of the 2-[(2,4-dichlorophenyl)methyl]-4,4-dimethyl-3-isoxazolidinone compound (Formula I) to the solvent A is 1:15-20; the solvent A is first heated to 60° C.-90° C., cooled to −5° C. to 5° C. for 15-20 hours, and re-heated to 15° C.-30° C.; and the volatilization process lasts for 10 to 20 days. The inventors discovered surprisingly that the crystals obtained from such technical protocol were a mixture of acicular crystals on the layer outside and rhombohedral crystals inside. The acicular crystals were collected and its melting point was determined to be 83.8° C. by differential scanning calorimetry (DSC).

When the monoclinic crystal of the 2-[(2,4-dichlorophenyl)methyl]-4,4-dimethyl-3-isoxazolidinone compound (Formula I) is dissolved in chloroform, hexane, methanol, ethyl acetate, toluene, acetone, DMF/water, DMSO/water, and other solvents/mixed solvents under similar conditions as above, an oily substance or a mixed solid with a long melting range is obtained, but the acicular crystal is not formed.

Another object of the application is to determine and provide a crystal form of the acicular crystal of the 2-[(2,4-dichlorophenyl)methyl]-4,4-dimethyl-3-isoxazolidinone compound (Formula I). A measurement of the acicular crystal using a single-crystal X-ray diffractometer shows that the crystal form of the 2-[(2,4-dichlorophenyl)methyl]-4,4-dimethyl-3-isoxazolidinone compound (Formula I) is an orthorhombic crystal. Table 1 specifically shows the lattice parameters of the orthorhombic crystal:

TABLE 1

Crystallographic parameters of the orthorhombic crystal by single-crystal X-ray diffraction

| Parameters | Orthorhombic crystal |
|---|---|
| Space group | P21 21 21 |
| a | 9.2301 (2) |
| b | 11.0751 (3) |
| c | 12.7554 (3) |
| α | 90 |
| β | 90 |
| γ | 90 |
| Volume | 1303.91 (5) Å 3 |
| Density | 1.396 g/cm3 |
| z | 4 |
| R, wR$^2$ | 0.0331, 0.0784 |

The parameters are defined as follows:
a, b, and c=side length of lattices;
α, β, and γ=angles of the lattices; and
Z=number of molecules in the lattices.

Figure 4:
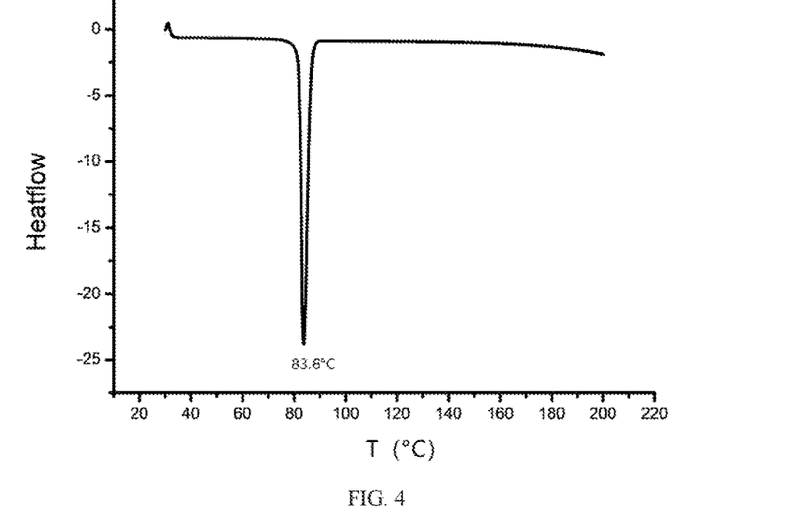
FIG. 4: DSC analysis diagram of an orthorhombic crystal form.

At 25° C., the orthorhombic crystal of the 2-[(2,4-dichlorophenyl)methyl]-4,4-dimethyl-3-isoxazolidinone compound (Formula I) has a X-ray powder diffraction (PXRD) reflex illustrated in FIG. 4 and diffraction parameters (2θ) shown in Table 2. Preferably, the diffraction parameters (2θ) consist of at least 3 in Table 2, less preferably at least 4, more preferably at least 5, and the most preferably all:

TABLE 2

PXRD parameters of the orthorhombic crystal
Orthorhombic crystal

| 2θ(°) | No. |
|---|---|
| 2θ = 10.53 ± 0.2 | (1) |
| 2θ = 14.20 ± 0.2 | (2) |
| 2θ = 15.92 ± 0.2 | (3) |
| 2θ = 18.5 ± 0.2 | (4) |
| 2θ = 19.80 ± 0.2 | (5) |
| 2θ = 21.10 ± 0.2 | (6) |
| 2θ = 24.92 ± 0.2 | (7) |
| 2θ = 27.73 ± 0.2 | (8) |

Herein, the PXRD is an experimentally observed diffraction pattern or a parameter derived therefrom. The PXRD pattern is characterized by a peak position (x-axis) and a peak intensity (y-axis).

A further object of the application is to investigate stability of the orthorhombic crystal of the 2-[(2,4-dichlorophenyl)methyl]-4,4-dimethyl-3-isoxazolidinone compound (Formula I). The orthorhombic crystal is stored in a high-temperature (60±2° C.) oven, in a 90±5% humidity condition, and under 4500±500l ux light intensity for 10 days, respectively, during which samples are collected on the 5th and 10th days for a PXRD analysis. As the analysis turns out, the orthorhombic crystal shows consistent 2θ angle values in the PXRD pattern before and after storage, indicating that the orthorhombic crystal is a stable crystal form under high temperature, humidity and light intensity conditions.

Still, a further object of the application is to provide a method for efficiently preparing the orthorhombic crystal of the 2-[(2,4-dichlorophenyl)methyl]-4,4-dimethyl-3-isoxazolidinone compound (Formula I), comprising the following steps:

Crude products of the 2-[(2,4-dichlorophenyl)methyl]-4,4-dimethyl-3-isoxazolidinone compound (Formula I) prepared by various methods are dissolved in solvent B, completely dissolved by heating the solvent B to 40-100° C., then cooled to 10-30° C. During the cooling process, the orthorhombic seed crystal of the compound (Formula I) is added to induce crystallization. A high-purity thermostable orthorhombic crystal product is obtained by filtration. The said crude products are oily liquid (content>80%) or solid (such as a monoclinic crystal with a melting point of 45° C.). The solvent B is one or more selected from the group consisting of alkanes, cycloalkanes, halogenated hydrocarbons, aromatic hydrocarbons, ethers, alcohols, esters, ketones, sulfoxides, amide solvents, and water; preferably one or more selected from the group consisting of alkanes, halogenated hydrocarbons, aromatic hydrocarbons, alcohol solvents, and water; and more preferably one or more selected from the group consisting of petroleum ether, toluene, chloroform, ethanol, and water. A weight/volume ratio of the 2-[(2,4-dichlorophenyl)methyl]-4,4-dimethyl-3-isoxazolidinone compound (Formula I) to solvent B is 1:0.5-3. The orthorhombic crystal of the 2-[(2,4-dichlorophenyl)methyl]-4,4-dimethyl-3-isoxazolidinone compound (Formula I) prepared therefrom has a purity greater than 99%.

Still, another object of the application is to provide an application of the orthorhombic crystal in preparation of agrochemical formulations. The orthorhombic crystal may be pre-formulated or used in combination with an inert additive. The orthorhombic crystal according to the application may be processed into a formulation known in the art to which the application pertains, such as a solution, an emulsion, a suspension, a powder, a foam, a paste, a granule, an aerosol and a microcapsule, as well as a polymer and a coating composition used for seeds, and a thermally aerosolized formulation.

The inert additive comprises a solid carrier or a liquid carrier, and may further comprise a surfactant, such as a wetting agent, a dispersant, a viscosity-modifying additive (thickener), a defoamer, an antifreeze agent, a pH reagent, a stabilizer, and a preservative.

The wetting agent is selected from calcium/sodium alkylbenzene sulfonate, calcium/sodium alkyl sulfate, and alcohol ethers.

The dispersant is selected from a lignins, sulfonates, phosphate esters, carboxylate polymers, and EO-PO block copolymers.

A filler is selected from bentonite, kaolin, white carbon black, attapulgite, and aluminium-magnesium silicate.

The viscosity-modifying additive (thickener) is selected from polyvinylpyrrolidone, Arabic gum, xanthan gum, carboxymethylcellulose sodium, polyvinyl alcohol, sodium alginate, and guar gum.

The defoamer is selected from silicones, C8-C10 fatty alcohols, C10-C20 saturated fatty acids and ester ethers.

The antifreeze agent is selected from ethylene glycol, glycerol, polyethylene glycol, urea, and sorbitol.

The preservative is selected from propionic acid, sodium propionate, sorbic acid, sodium sorbate or potassium sorbate, benzoic acid, sodium benzoate, p-hydroxybenzoic acid sodium salt, methyl p-hydroxyphenyl ester, and isothiazolinone.

The stabilizer is selected from bentonite, white carbon black, and light calcium carbonate.

In an embodiment, the orthorhombic crystal may be conveniently and directly prepared into a 40% SC formulation. A preparation method comprises the following steps: mixing the orthorhombic crystal with Borresperse CA (lignosulfonate), Ethyl an 324 (EOPO block copolymer), SAG1572 (silicone), kelzan S-PLUS (xanthan gum), ethylene glycol and water at a ratio of the formula, and grinding with a sand mill to obtain the 40% SC formulation.

In another embodiment, the orthorhombic crystal may be conveniently and directly prepared into a 40% WG formulation. The preparation method comprises the following steps: mechanically pulverizing, kneading, granulating and drying the orthorhombic crystal, Stepanol DX-165N (sodium dodecyl sulfate), Morwet D-425 (naphthalene sulfonate condensate), Borresperse CA (lignosulfonate), AGNIQUE Soap-L (sodium tallowate) and TS-1 (kaolin) to obtain the 40% WG formulation.

It is worth noting that the process by which the orthorhombic crystal containing the compound (Formula I) is made into the WG formulation has not been reported in the technical field to which the application pertains.

Also, another object of the application is to provide an application of the orthorhombic crystal in weed control.

When used as a herbicide, the orthorhombic crystal may be 0.01% to 99% by weight. The orthorhombic crystal may be combined with one or more herbicides (Compound A for short) to exert a synergistic effect, expand a weed control spectrum, prevent occurrence of resistance or raise crop safety. When used in combination with other herbicides, the orthorhombic crystal may be formulated with Compound A or applied sequentially with Compound A. Compound A is selected from:

A.1 ALS inhibitor,
A.2 ACCase inhibitor,
A.3 PPO inhibitor,
A.4 HPPD inhibitor or
A.5 Others, including a carotenoid biosynthesis inhibitor, a cell division and growth inhibitor, an auxin transport inhibitor, a plant growth regulator and a herbicide safener.

Compound A is specifically selected from fenoxaprop-p-ethyl, clodinafop-propargyl, diclofop-methyl, thiobencarb, triallate, pendimethalin, trifluralin, metazachlor, propyzamide, s-metolachlor, tebuthiuron, diuron, isoproturon, 2,4-D, chipton, fluroxypyr (isooctyl ester), dicamba, bentazone, carfentrazone-ethyl, florasulam, tribenuron-methyl, chlorsulfuron, amidosulfuron, cyclosulfamuron, flucarbazone-sodium, mesosulfuron-methyl, diquat, paraquat, and glyphosate (isopropylamine salt).

When used as a herbicide, the compound (Formula I) or the combination may be applied together with a safener to raise crop safety. The safener is selected from naphthalic anhydrides, dichloroacetamides, oxime ethers, heterocycles, sulfonylureas (sulfonamides), plant growth regulators, and fungicides. The safener is specifically selected from 1,8-Naphthalic anhydride, dichlormid, Benoxacor, Furilazde, flurazole, phthalic acid, bromophthalic anhydride, femclorim, benoxacor, cyometrinil, R25788, and MG191.

The orthorhombic crystal of the 2-[(2,4-dichlorophenyl)methyl]-4,4-dimethyl-3-isoxazolidinone compound (Formula I) may be used for weed control in crops like corn, wheat, rape, rice, sorghum, barley or rye. Weeds in a corn mays field mainly comprise *Echinochloa crus-galli, Digitaria sanguinalis, Setaria viridis, Eleusine indica, Cynodon dactylon, Phragmites australis, Cyperus iria, Polygonum L., Xanthium sibiricum, abutilon, Solanum nigrum, Chenopodiaceae, Acalypha australis, Malachium aquaticum, Ama-* ranthus retroflexus, Portulaca oleracea, Amaranthus blitum, Conyza Canadensis, Elsholtzia ciliata, Cirsium japonicum, Cirsium setosum, Sonchus oleraceus L., Eclipta prostrata, Calystegia hederacea, Parthenocissus tricuspidata, Commelina communis, Capparis spinosa L., Plantago asiatica, Medicago sativa L., and Glycine soja.

Weeds in a wheat field mainly comprise *Alopecurus aequalis, Alopecurus japonicus, Beckmannia syzigachne, Bromus japonicus Thunb, Poa annua, Avena fatua, Polypogon, Lolium perenne, Aegilops tauschii, Stellaria uliginosa, Galium spurium, Stellaria media, Cerastium arvense, Veronica didyma, Cardamine hirsuta, Polygonum lapathifolium, Vicia sativa, Capsella bursa-pastoris, Ixeris denticulata, Hemistepta lyrata, Oxalis corniculata, Euphorbia helioscopia, Convolvulus arvensis, Silene conoidea, Chenopodiaceae serotinum L., Polygonum aviculare L., Rumex dentatus, Thlaspi arvense, Lapsana apogonoides, Lamium amplexicaule,* and *Rotala indica.*

Other weeds comprise *Abutilon theophrasti,* AstilberivularisBuch.-Ham. ex D. Don., *Ambrosia artemisiifolia, Leymus chinensis, Lolium multiflorum, Datura stramonium, Sorghum halepeme, Pharbitis* Choisy, *Elytrigia, Helianthus annuus, Polygonum convolvulus, Sinapis arvensis, Setaria glauca,* green foxtail, *Chenopodium album, Commelina benghalensis, Nigella damascena, Brachiara eruciformis, Cirsium arvense, Xanthium pensylvanicum, Papaver rhoeas, Matthiola incana, Setaria viridis* sp. *Pycnocoma,* hairy beggarticks, *Nigella damascena,* horseweed, largecrabgrass, littleseed canarygras, Pennsylvaniasmartweed, pitted morningglory, *Sida spinosa* L., *Apera spica-venti,* wild poinsettia and *Cyperus esculentus.*

In an embodiment, a SC formulation containing the orthorhombic crystal of the compound (Formula I) shows a herbicidal activity of 100% against *Stellaria media* and 97% against *Poa annua* L. at 62.5 g ai/ha. These data prove that the SC formulation containing the orthorhombic crystal of the compound (Formula I) according to the application presents a considerably higher herbicidal activity and a much better weed control effect than a control medicament (Command, commercially available) and its homogeneous liquid formulations (such as an emulsifiable concentrate (EC) formulation). Meanwhile, the embodiment shows that the SC is safer for crops such as corn and wheat: when the SC formulation is applied at an active ingredient dose of 500 g ai/ha, crop growth is only slightly affected.

In another embodiment, a WG formulation containing the orthorhombic crystal of the compound (Formula I) shows a herbicidal activity of 100% against *Stellaria media* and 97% against *Poa annua* L. at a dose of 62.5 g ai/ha. These data prove that the WG containing the orthorhombic crystal of the compound (Formula I) according to the application presents a considerably higher herbicidal activity and a much better weed control effect than the control agent (Command, commercially available) and its homogeneous liquid formulations (such as the EC formulation). It is worth pointing out that compared with the SC formulation, the WG formulation maintains an effective herbicidal activity at a low dose. For example, the herbicidal activity of the WG formulation remains above 80%, while the dose is reduced to 15.625 g ai/ha. The WG formulation is nearly as safe as the SC formulation for crops such as corn and wheat.

The following are advantageous effects of the application:
(1) The orthorhombic crystal of the 2-[(2,4-dichlorophenyl)methyl]-4,4-dimethyl-3-isoxazolidinone compound (Formula I) with a melting point of 83° C.-85° C. according to the application is a photostable, moisture-stable, and thermostable crystal, wherein the orthorhombic crystal may be stored simply and conveniently at room temperature, while crystal transformation does not occur, hence no negative effects on further processing and applications.
(2) The method for preparing the orthorhombic crystal of the 2-[(2,4-dichlorophenyl)methyl]-4,4-dimethyl-3-isoxazolidinone compound (Formula I) according to the application is convenient and efficient, wherein an oil crude product (80% content) or a sub-thermal stable crystal (with a melting point of 45° C.) of the compound (Formula I) prepared by various methods can be efficiently converted by the method of the application into the stable orthorhombic crystal, which is suitable for large-scale industrial production.
(3) The orthorhombic crystal of the compound (Formula I) according to the application may be conveniently and directly used in preparation of agrochemical formulations, especially green and environmentally friendly solid formulations such as the SC formulation and the WG formulation, overcoming the issues encountered when an oily/low-melting-point sub-thermally stable active ingredient is directly processed into a solid-containing formulation.
(4) The solid formulations (such as the SC formulation and the WG formulation) prepared with the orthorhombic crystal of the compound (Formula I) according to the application has a higher herbicidal activity, especially the WG formulation, which is environmentally friendly and produce a desired herbicidal effect with a lower dosage and reduce herbicide cost, compared with a homogeneous liquid formulation (such as the EC).
(5) The solid formulations (such as the SC formulation and the WG formulation) prepared with the orthorhombic crystal of the compound (Formula I) according to the application significantly improve safety of crops (such as corn and wheat) as a herbicide.

DETAILED DESCRIPTION OF THE PREFERRED EMBODIMENTS

The following embodiments further illustrate the features of the application, but are not intended to limit the content and scope of the application.

A DSC (TA (Du Pont) Instruments) is employed to collect information and raise the temperature of a sample from 30° C. to 200° C. with a ramp rate of 10° C./min.

A single crystal X-ray diffractometer (Gemini A Ultra, Agilent, USA) is employed to scan Cu-Kα rays and collect single crystal data in a ω/2θ mode.

A PXRD diffractometer (X'Pert PRO, PNAlytical, Netherlands) is employed to collect the following specific data: Cu anode=40 kV, 150 mA, 2θ scanning range=0°~45°, scanning speed=8°/min, step size=0.02°, divergence slit (DS)=1°, anti-scattering slit=(SS) 1°, and receiving slit (RS)=0.15 mm.

Embodiment 1 (Using a Preparation Method Disclosed in U.S. Pat. No. 4,405,357)

100 g of 2,4-dichlorobenzaldehyde is dissolved with 500 mL of ethanol in a 1-L three-necked flask under stirring. 79.4 g of hydroxylamine hydrochloride is added in portions at 20° C. After addition, the mixture is heated to 30° C., 230 g of a 20% sodium hydroxide solution is added dropwise in 30 minutes, while the temperature reaches to 45° C. After addition, the mixture is stirred for 1.5 hours, cooled, added slowly to 500 mL of water and stirred for 1 hour, filtered and dried under vacuum to produce 103 g of 2,4-dichlorobenzaldoxime solid.

The 2,4-dichlorobenzaldoxime solid obtained above is dissolved in 1000 mL of methanol at 20° C. A solution containing 42.2 g of sodium cyanoborohydride and 1 mL colorant of 1-ethyl-2-[3-(1-ethylnaphtho[1,2-d]thiazol-2 (1H)-ylidene)-2-methyl-1-propen-1-yl]-n aphtho[1,2-d]thiazolium bromide in 700 mL methanol and 314 mL solution of hydrochloric acid solution (2N) in methanol are added dropwise simultaneously while maintaining the reaction mixture acidic. After additions are complete, the mixture is stirred at room temperature for 1.5 hours. Methanol is removed under reduced pressure, water is added. The mixture is stirred, filtered, washed with water and dried to give 67.4 g of N-[(2,4-dichlorophenyl)methyl]hydroxylamine solid.

Under an inert atmosphere, 600 mL of a dichloromethane solution containing 67.4 g of the N-[(2,4-dichlorophenyl) methyl]hydroxylamine solid is mixed with 97 g of pyridine at –10° C., and 42 g of trimethylchlorosilane is slowly added in portions while stirring. After addition is complete, the mixture is stirred at –10° C. for 30 minutes and then warmed to 0° C., a solution 35.6 g of 3-chloro-2,2-dimethylpropanoyl chloride in 30 mL of dichloromethane is added dropwise in 20 minutes, stirred at room temperature for 18 hours. After the reaction is complete, the organic layer is separated, washed with water, acid, brine and dried. Removal of solvent gives 24.5 g of 3-chloro-N-(2,4-dichlorophenyl)methyl-N-hydroxyl-2,2-dimethylpropionamide.

24.5 g of 3-chloro-N-(2,4-dichlorophenyl)methyl-N-hydroxyl-2,2-dimethylpropionamide obtained above is dissolved in 500 mL of methanol. 5.26 g of 85% potassium hydroxide solution is added. The reaction mixture is stirred at room temperature for 18 hours, and filtered. The solvent is removed under reduced pressure. Water is added, the aqueous solution is extracted twice with 300 mL of dichloromethane. The organic layers are combined, dried over anhydrous sodium sulfate, filtered, and concentrated under reduced pressure to give 17.5 g of oily substance of the 2-[(2,4-dichlorophenyl)methyl]-4,4-dimethyl-3-isoxazolidinone compound (Formula I), with content of 75% as determined by gas chromatography (GC).

Embodiment 2 (Using a Method Disclosed in Patent CN201910188658.2)

23 g of 4,4-dimethyl-3-isoxazolidinone is dissolved in 200 mL of DMF solvent. 25 g of sodium carbonate is added. The mixture is heated to 75° C., and water is removed by distillation under reduced pressure until water content is below 0.1%. 39 g of 2,4-dichlorobenzyl chloride is added dropwise. After the reaction is complete, the mixture is stirred for 2 hours at 75° C., the solvent is removed under reduced pressure, dichloromethane and water are added. The phases are separated. The solvent of organic layer is removed to give 55 g of oily crude product of the 2-[(2,4-dichlorophenyl)methyl]-4,4-dimethyl-3-isoxazolidinone compound. As determined by the GC, in addition the main target product (92%), there is about 2% of 2,4-dichlorobenzyl chloride.

Figure 1:
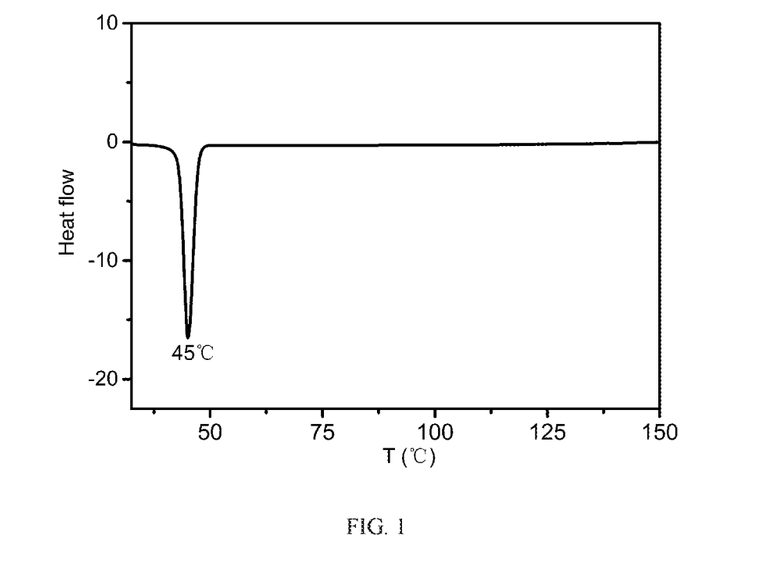
FIG. 1: DSC analysis diagram of a monoclinic crystal form.

55 g of the crude product obtained above is dissolved in 95 mL of isopropanol. The mixture is cooled to –15° C., and 5 mL water is added slowly. The crystal formed is filtered to give 50 g of white solid product. As determined by GC, the content of the target product is 99.1% with a melting point of 45° C., while the 2,4-dichlorobenzyl chloride is below the detection limit (see FIG. 1 for DSC data). 1H NMR (500 MHz, CDCl$_3$) δ7.40 (d, J=2.0 Hz, 1H), 7.28 (d, J=8.3 Hz, 1H), 7.24 (dd, J=8.3, 2.0 Hz, 1H), 4.79 (s, 2H), 4.01 (s, 2H), 1.26 (s, 6H).

Figure 2:
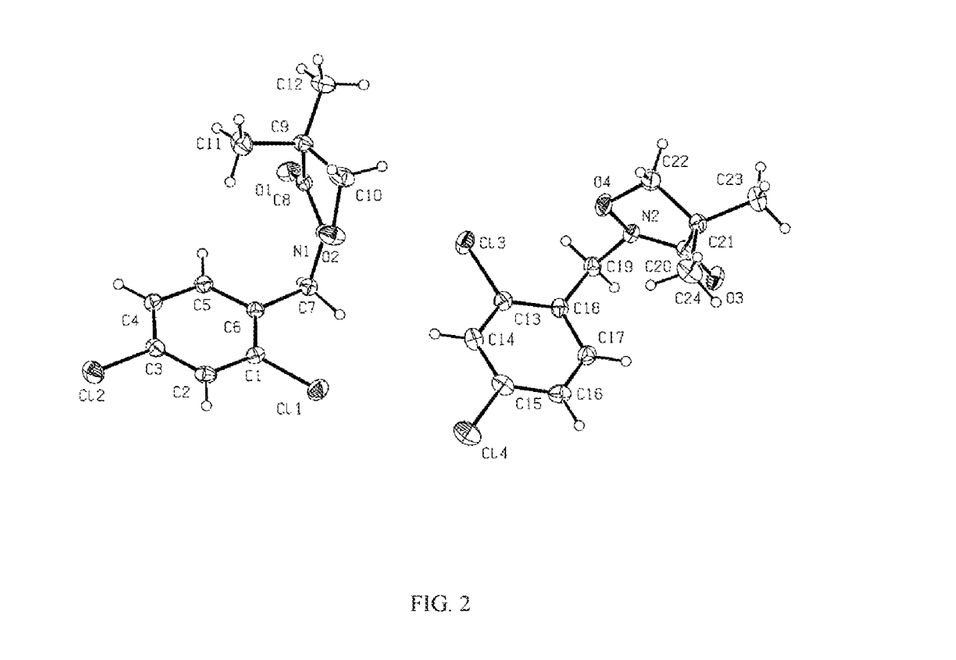
FIG. 2: Structure diagram of the monoclinic crystal form by single-crystal X-ray diffraction.
Figure 3:
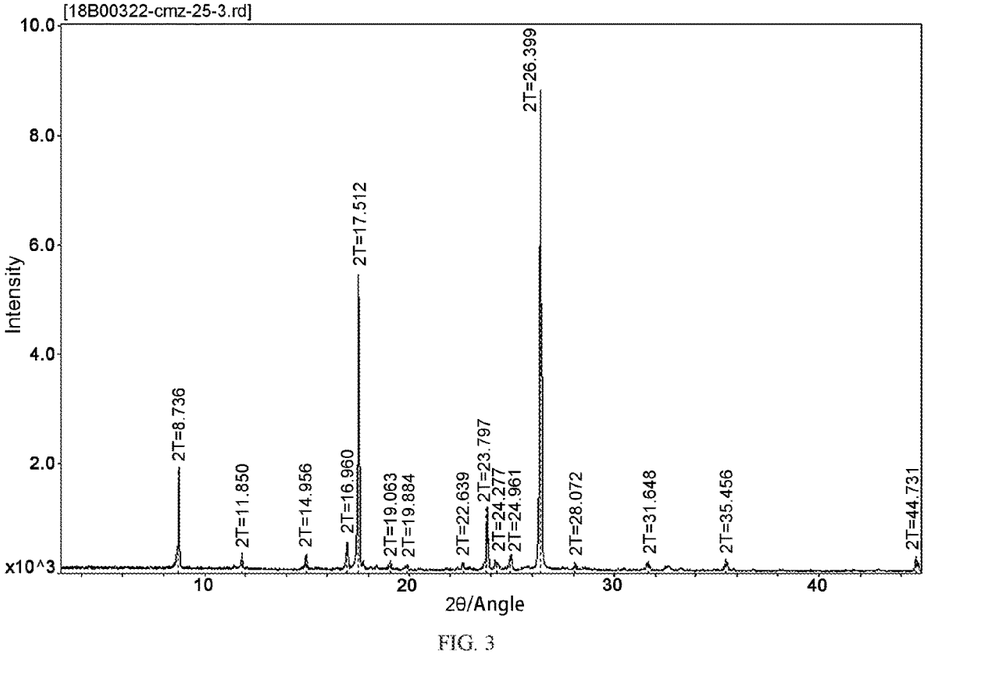
FIG. 3: PXRD diagram of the monoclinic crystal form.

The PXRD indicates that the 2-[(2,4-dichlorophenyl) methyl]-4,4-dimethyl-3-isoxazolidinone (Formula I) is a crystalline compound (FIG. 3). The single crystal X-ray diffraction further indicates that the 2-[(2,4-dichlorophenyl) methyl]-4,4-dimethyl-3-isoxazolidinone (Formula I) is in a monoclinic crystal structure (FIG. 2).

Embodiment 3

The monoclinic crystal (500 mg, melting point 45° C.) of the 2-[(2,4-dichlorophenyl)methyl]-4,4-dimethyl-3-isoxazolidinone compound (Formula I) obtained in Embodiment 2 is mixed with 10 mL of petroleum ether (boiling range 60° C.-90° C.), heated to reflux, then cooled to 0° C. for 18 hours. The mixture is kept at room temperature for 20 days, slowly volatilized, and crystallized to give a mixture of acicular crystals on the layer outside and rhombohedral crystals inside. The acicular crystals on the layer outside are collected to give 300 mg of the crystal. The content is 99.8% of the crystal as determined by GC, with the melting point of 83.8° C. (see FIG. 4 for DSC data).

Figure 5:
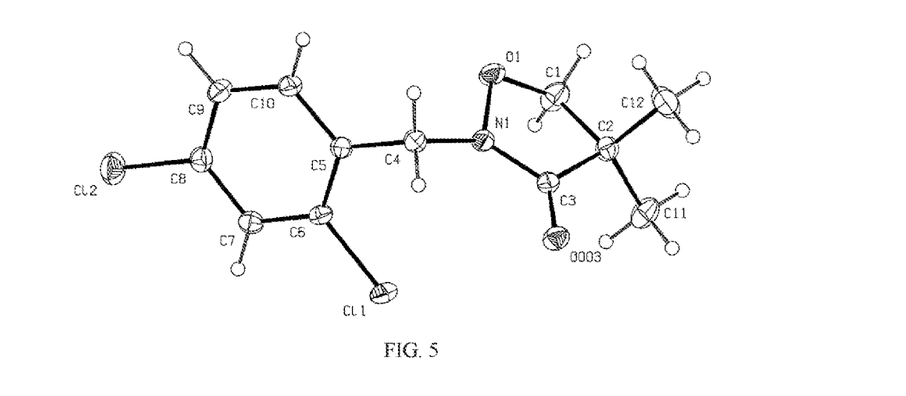
FIG. 5: Structure diagram of the orthorhombic crystal form by single-crystal X-ray diffraction.
Figure 6:
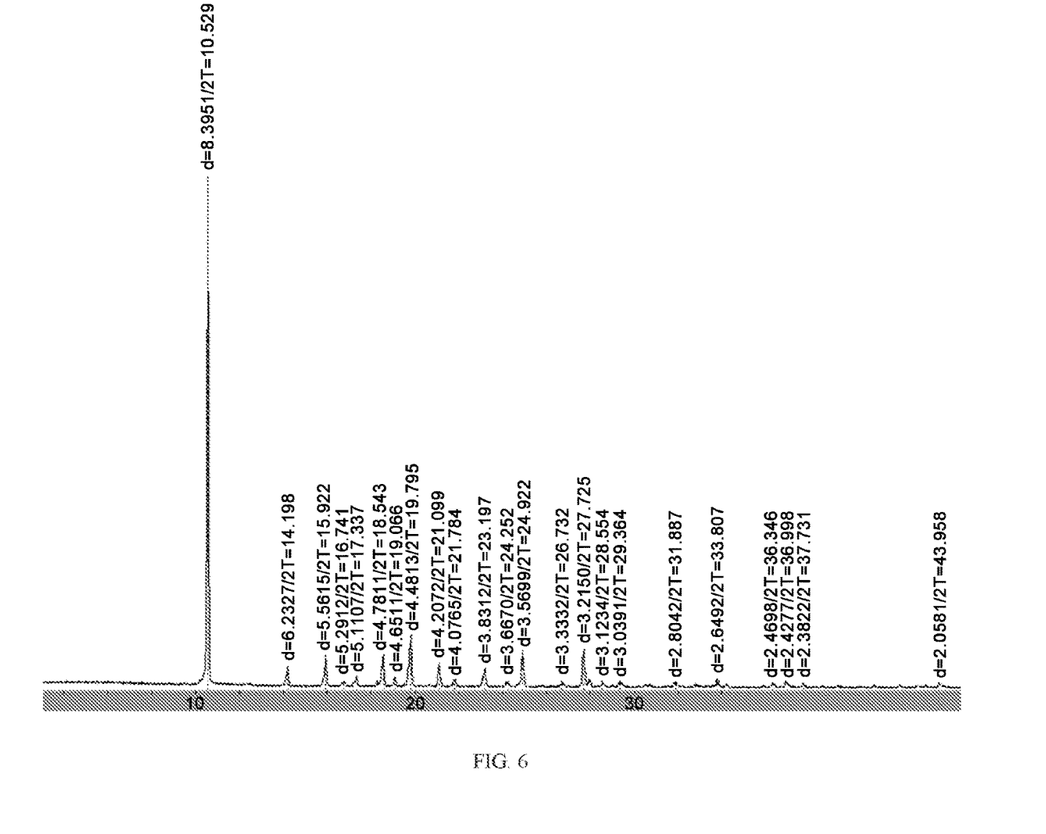
FIG. 6: PXRD diagram of the orthorhombic crystal form.

The PXRD indicates that the 2-[(2,4-dichlorophenyl) methyl]-4,4-dimethyl-3-isoxazolidinone (Formula I) is the crystalline compound (FIG. 6). The single crystal X-ray diffraction further indicates that the 5-[(2,4-dichlorophenyl) methyl]-4,4-dimethyl-3-isoxazolidinone (Formula I) is in an orthorhombic crystal structure (FIG. 5), with lattice parameters shown in Table 1.

Embodiment 4

The monoclinic crystal (20 g) of the 2-[(2,4-dichlorophenyl)methyl]-4,4-dimethyl-3-isoxazolidinone compound (Formula I) obtained in Embodiment 2 is dissolved in a 10 mL solvent prepared by mixing petroleum ether with toluene at a volume ratio of 10:1. The mixture is heated to 60° C. and refluxed for 3 hours. The mixture is cooled to room temperature of 25° C. After removing about ⅓ volume of the solvent, the mixture is cooled to room temperature, while 10 mg of the crystal obtained in Embodiment 3 is added. The mixture is stirred and the crystal is filtered to give 17 g of white solid product, with content of 99.3% as determined by GC and melting point of 84.5° C. PXRD data are consistent with the data of Embodiment 3.

Embodiment 5

The oily substance (15 g) of the 2-[(2,4-dichlorophenyl) methyl]-4,4-dimethyl-3-isoxazolidinone compound (Formula I) obtained in Embodiment 1 is dissolved in 15 ml of ethanol. The mixture is heated to 78° C., slowly cooled to 10° C. while 10 mg of the crystal from Embodiment 3 is added. The mixture is stirred and crystal is filtered to give 12.1 g of white solid product, with content of 98.5% determined by GC and melting point of 83° C. PXRD data are consistent with the data of Embodiment 3.

Embodiment 6

The oily substance (10 g) of the 2-[(2,4-dichlorophenyl)methyl]-4,4-dimethyl-3-isoxazolidinone compound (Formula I) obtained in Embodiment 1 is dissolved in 25 ml of chloroform. The mixture is heated to 60° C., slowly cooled to room temperature while 10 mg of the crystal from Embodiment 3 is added. The mixture is stirred for 30 minutes and crystal is filtered to give 8 g of white solid product, with content of 99% as determined by GC and melting point of 83.5° C. PXRD data are consistent with the data of Embodiment 3.

Embodiment 7

The oily substance (10 g) of the 2-[(2,4-dichlorophenyl)methyl]-4,4-dimethyl-3-isoxazolidinone compound (Formula I) obtained in Embodiment 1 is dissolved in 25 ml of ethanol. The mixture is heated to reflux for 1 hour, slowly cooled to room temperature while 10 mg of the crystal from Embodiment 3 is added. The mixture is stirred for 30 minutes. No crystal is precipitated.

Embodiment 8 Stability Experiment of the Orthorhombic Crystal of the 2-[(2,4-dichlorophenyl)methyl]-4,4-dimethyl-3-isoxazolidinone Compound (Formula I)

The crystals of the 2-[(2,4-dichlorophenyl)methyl]-4,4-dimethyl-3-isoxazolidinone compound (Formula I) obtained in embodiments 3, 4, 5, and 6 are respectively placed in a high-temperature (60±2° C.) oven, in a 90±5% humidity condition, and under 4500±5001 ux light intensity for 10 days. Samples are collected on the 5th and 10th days for the PXRD analysis.

Based on PXRD data, the orthorhombic crystals show consistent 20 angle values before and after storage, indicating that the orthorhombic crystals are stable crystal form that remain stable under high temperature, high humidity, and light intensity.

Embodiment 9 Preparation of 40% SC formulation of the 2-[(2,4-dichlorophenyl)methyl]-4,4-dimethyl-3-isoxazolidinone Compound (Formula I)

The 40% SC formulation of the 2-[(2,4-dichlorophenyl)methyl]-4,4-dimethyl-3-isoxazolidinone compound is prepared by mixing the active ingredient, dispersant, wetting agent, defoamer, thickener, antifreeze and water listed in the following table at a ratio of the formula, and processing on the sand mill.

| Ingredients | Grades | % |
| --- | --- | --- |
| 2-[(2,4-dichlorophenyl)methyl]-4,4-dimethyl-3-isoxazolidinone | | 40% |
| Lignosulfonate | Borresperse CA | 4% |
| EOPO block copolymer | Ethylan 324 | 2% |

-continued

| Ingredients | Grades | % |
| --- | --- | --- |
| Silicone | SAG1572 | 0.3% |
| Xanthan gum | kelzan S-PLUS | 0.1% |
| Ethylene glycol | | 2% |
| Water | | Make up 100% |

The inventors surprisingly discovered that the new SC formulation obtained above meets the physical and chemical property requirements of a conventional SC formulation, and no degradation or increase in particle size occurs during storage.

| Experiment items | Experiment results |
| --- | --- |
| Content, % | 39.13% |
| Content (54° C., 14 days) | 39.10% |
| Suspension rate, % | 95.46 |
| PH (MT75.2) | 8.51 |
| Persistent foaming, mL, 1 min | 0 |
| Particle size, D90, μm | 5.1 |
| Particle size, D90, μm (54° C., 14 days) | 5.3 |

Embodiment 10 Preparation of 40% WG Formulation of the 2-[(2,4-dichlorophenyl)methyl]-4,4-dimethyl-3-isoxazolidinone Compound (Formula I)

The 40% WG formulation of 2-[(2,4-dichlorophenyl)methyl]-4,4-dimethyl-3-isoxazolidinone is prepared by evenly mixing the ingredients listed in the following table at the ratio of the formula, mechanical pulverizing, kneading, granulating and drying.

| Ingredients | Grades | % |
| --- | --- | --- |
| 2-[(2,4-dichlorophenyl)methyl]-4,4-dimethyl-3-isoxazolidinone | | 40% |
| Sodium dodecyl sulfate | stepanolDX-165N | 3% |
| Naphthalene sulfonate condensate | Morwet D-425 | 4% |
| Lignosulfonate | Borresperse CA | 4% |
| Sodium tallowat | AGNIQUE Soap-L | 0.5% |
| Kaolin | TS-1 | Make up100% |

The new WG formulation obtained above is analyzed, the quality meets the physical and chemical property requirements of a conventional WG formulation.

Embodiment 11 Preparation of 25% EC Formulation of the 2-[(2,4-dichlorophenyl)methyl]-4,4-dimethyl-3-isoxazolidinone Compound (Formula I)

A transparent and uniform liquid is prepared by placing 25 g of the orthorhombic crystal according to Embodiment 3 in a reaction flask, adding the additives shown in the following table, and stirring evenly at 30° C., wherein the content of 2-[(2,4-dichlorophenyl)methyl]-4,4-dimethyl-3-isoxazolidinone is 25% and remains unchanged when stored at 54° C.; and 2 mL of foam is produced without free oil or emulsifiable paste at 2 h while no foam, free oil, or emulsifiable paste is produced at 24 h.

| Ingredients | Grades | % |
| --- | --- | --- |
| 2-[(2,4-dichlorophenyl)methyl]-4,4-dimethyl-3-isoxazolidinone | | 25% |
| Styryl ethoxy compound | TS160 | 8% |
| Calcium dodecylbenzene sulfonate | CAL | 5% |
| Mineral oil | Solvesso 150 | 62% |

Embodiment 12 Biological Activity Experiment of the Orthorhombic Crystal of the 2-[(2,4-dichlorophenyl)methyl]-4,4-dimethyl-3-isoxazolidinone Compound (Formula I)

Experiment target: *Stellaria media* and *Poa annua* L. are the experiment targets for a herbicidal activity evaluation, whose weed seeds are collected in fields and stored indoors. The experiment targets for a crop safety evaluation are wheat (*Triticum aestirum*) and corn (*Zea mays*), whose seeds are purchased from a seed company.

Liquid preparation: a certain quality of medicine is accurately taken and diluted with clear water containing 0.1% Tween 80 emulsifier to prepare a formulation with a specified concentration, and then the formulation is directly diluted with distilled water.

In a greenhouse pot experiment, a plastic pot is filled with a specified quantity of soil, and 15-20 seeds of target weeds are sown on a surface of the soil, covered with 0.5-1 cm of fine soil and cultured in a greenhouse for 24 hours. A soil spray application experiment is conducted through pre-emergent soil spraying processes, where crops and weeds are sprayed with the SC, WG, and EC formulations according to embodiments 9, 10, and 11 at effective doses of 15.625, 31.25, 62.5, 250, 375, and 500 g ai/ha, with each process repeated 3 times. The soil not subjected to the formulations is taken as a blank control group, with a Clomazone SC formulation (Command, 360 g/L, commercially available) as a control agent. The blank control group is sprayed with clean water and then cultured in the greenhouse. A routine observation is performed on growth of the target crops, and an evaluation via visual inspection is carried out for a comprehensive growth inhibition rate of the control agent 30 days after spraying. The growth inhibition rate is evaluated by crop damage symptoms (inhibition, deformity, yellowing, and bleaching), wherein 0 means no growth effect, and 100% means complete inhibition of crop growth. The following are evaluation criteria for the herbicidal activity and the crop safety by a visual inspection method.

| Control rate (%) | Herbicidal activity | Crop safety |
| --- | --- | --- |
| 0 | No effect | No crop reduction or loss |
| 10 | Slight effect | Slight discoloration or shortness |
| 20 | | Partial discoloration, dwarfing or crop loss |
| 30 | | More significant but not persistent crop damage |
| 40 | Moderate effect | Moderate damage, where crops may usually recover |
| 50 | | More persistent drop damage, making it difficulty for crops to recover |
| 60 | | Persistent crop damage, making it impossible for crops to recover |
| 70 | Severe effect | Severe crop damage and plant loss |
| 80 | | A majority of crops are destroyed and only a few survive |
| 90 | | Only scattered crops survive |
| 100 | Full effect | All crops are destroyed |

Experiment 1: A herbicidal activity experiment on the control agent (Command), the EC formulation in Embodiment 11, the SC formulation in Embodiment 9, and the WG formulation in Embodiment 10.

| | Effective doses | Herbicidal activity (%) | |
| --- | --- | --- | --- |
| Process | g a.i./ha | Stellaria media | Poa annua L. |
| Control agent | 15.625 | 50 | 10 |
| | 31.25 | 70 | 17 |
| | 62.5 | 100 | 60 |
| EC formulation in Embodiment 11 | 15.625 | 50 | 43 |
| | 31.25 | 65 | 70 |
| | 62.5 | 100 | 87 |
| SC formulation in Embodiment 9 | 15.625 | 53 | 50 |
| | 31.25 | 70 | 70 |
| | 62.5 | 100 | 97 |
| WG formulation in Embodiment 10 | 15.625 | 82 | 60 |
| | 31.25 | 83 | 82 |
| | 62.5 | 100 | 97 |

Based on the experiment results, the WG formulation of the 2-[(2,4-dichlorophenyl)methyl]-4,4-dimethyl-3-isoxazolidinone compound (Formula I) shows the highest herbicidal activity against *Stellaria media* (82%-100%) and *Poa annua* L. (60%-97%), followed by the SC formulation (53%-100% and 50%-97%) and the EC formulation (50%-100% and 43%-87%); The control agent has the lowest herbicidal activity, 50%-100% against *Stellaria media* and 10%-60% *Poa annua* L.

Experiment 2: A crop safety experiment on the control agent (Command), the EC formulation in Embodiment 11, the SC formulation in Embodiment 9, and the WG formulation in Embodiment 10.

| | Effective dose | Crop safety (%) | |
| --- | --- | --- | --- |
| Process | (g a.i./ha) | wheat | corn |
| Control agent | 500 | 100 | 5 |
| | 375 | 94 | 0 |
| | 250 | 93 | 0 |
| EC formulation in Embodiment 11 | 500 | 7 | 0 |
| | 375 | 0 | 0 |
| | 250 | 0 | 0 |
| SC formulation in Embodiment 9 | 500 | 13 | 11 |
| | 375 | 3 | 0 |
| | 250 | 0 | 0 |
| WG formulation in Embodiment 10 | 500 | 15 | 13 |
| | 375 | 11 | 3 |
| | 250 | 0 | 0 |

Based on the experiment results, the EC formulation of the 2-[(2,4-dichlorophenyl)methyl]-4,4-dimethyl-3-isoxazolidinone compound (Formula I) is the safest with growth inhibition rates of 0%-7% and 0% in wheat and corn, respectively, indicating almost no growth effect and high safety. The SC and WG formulations follow. The SC formulation shows the growth inhibition rates at 0%-13% and 0%-11% whereas the growth inhibition rates of the WG formulation are 0%-15% and 0-13%. Both produce slight growth effects and have good safety. The control agent has

93%-100% and 0-5% growth inhibition in wheat and corn, indicating good safety to corn but severe damage to wheat. It is thus evident that the 2-[(2,4-dichlorophenyl)methyl]-4,4-dimethyl-3-isoxazolidinone compound (Formula I) is safe to wheat and corn, with the EC, SC and WG formulations showing significantly higher safety to wheat than the control agent.

To put Experiment 1 and Experiment 2 together, the formulations prepared with the orthorhombic crystal of 2-[(2,4-dichlorophenyl)methyl]-4,4-dimethyl-3-isoxazolidinone present significantly higher activities than the control agent, wherein the SC and WG solid formulations are more herbicidally active than the EC formulation; and the EC, SC and WG formulations are safe to wheat and corn, significantly safer than the control agent especially in wheat. Compared with the control agent, the crystal form has better application and development prospects due to greater safety performance on the target crops and better weeding effect on the target weeds.

While the application has been described in detail with reference to the preferred embodiments thereof, the description is not meant to limit the application. Various modifications in the solution to problem may be made without departing from the technical scope of the application, which will fall within the scope of the claims.

What is claimed is:

1. A crystal of 2-[(2,4-dichlorophenyl)methyl]-4,4-dimethyl-3-isoxazolidinone compound (Formula I), wherein the crystal is an orthorhombic crystal, with a space group of P21 21 21 and lattice parameters of a=9.2301 (2) Å, b=11.0751 (3) Å, c=12.7554 (3) Å, α=90°, β=90°, and γ=90°;

(I)

2. The crystal of 2-[(2,4-dichlorophenyl)methyl]-4,4-dimethyl-3-isoxazolidinone compound (Formula I) according to claim 1, wherein the orthorhombic crystal shows, in X-ray powder diffraction reflexes determined as 2θ angle values using Cu-Kα radiation, at least three of the following reflexes:

(1) 2θ=10.53±0.2°;
(2) 2θ=14.20±0.2°;
(3) 2θ=15.92±0.2°;
(4) 2θ=18.54±0.2°;
(5) 2θ=19.80±0.2°;
(6) 2θ=21.10±0.2°;
(7) 2θ=24.92±0.2°; and
(8) 2θ-27.73±0.2.

3. The crystal of the 2-[(2,4-dichlorophenyl) methyl]-4,4-dimethyl-3-isoxazolidinone compound (Formula I) according to claim 1, wherein a melting point of the crystal ranges from 83° C. to 85° C.

4. A method for preparing a seed crystal of the crystal of the 2-[(2,4-dichlorophenyl)methyl]-4,4-dimethyl-3-isoxazolidinone compound (Formula I) according to claim 1, wherein a preparation process comprises dissolving a sub-thermostable monoclinic crystal of the 2-[(2,4-dichlorophenyl)methyl]-4,4-dimethyl-3-isoxazolidinone compound (Formula I) in organic solvent A, slowly volatilizing the solvent A through heating, cooling and re-heating, and then crystallizing; wherein the solvent A is one or more selected from the group consisting of alkanes and cycloalkanes.

5. A method for preparing a high-purity thermostable crystal of the 2-[(2,4-dichlorophenyl)methyl]-4,4-dimethyl-3-isoxazolidinone compound (Formula I) according to claim 1, wherein a preparation process comprises dissolving a crude product of the 2-[(2,4-dichlorophenyl)methyl]-4,4-dimethyl-3-isoxazolidinone compound (Formula I) in solvent B by heating the solvent B to 40-100° C., then cooling to 10-30° C. while adding an orthorhombic seed crystal of the 2-[(2,4-dichlorophenyl)methyl]-4,4-dimethyl-3-isoxazolidinone compound (Formula I) prepared according to the method of claim 4, crystallizing, and filtering to obtain a high-purity thermostable orthorhombic crystal; wherein the crude product is an oily liquid or solid; and wherein the solvent B is one or more selected from the group consisting of alkanes, cycloalkanes, halogenated hydrocarbons, aromatic hydrocarbons, ethers, alcohols, esters, ketones, sulfoxides, amide solvents, and water.

6. The method for preparing the high-purity thermostable crystal of the 2-[(2,4-dichlorophenyl)methyl]-4,4-dimethyl-3-isoxazolidinone compound (Formula I) according to claim 5, wherein content of 2-[(2,4-dichlorophenyl)methyl]-4,4-dimethyl-3-isoxazolidinone compound (Formula I) in the crude product is not less than 80%; wherein the solvent B is one or more selected from the group consisting of alkanes, halogenated hydrocarbons, aromatic hydrocarbons, alcohol solvents, and water; and wherein a weight/volume ratio of the 2-[(2,4-dichlorophenyl)methyl]-4,4-dimethyl-3-isoxazolidinone compound (Formula I) to solvent B is 1:0.5-3.

7. The method for preparing the high-purity, thermostable crystal of the 2-[(2,4-dichlorophenyl)methyl]-4,4-dimethyl-3-isoxazolidinone compound (Formula I) according to claim 6, wherein the solvent B is one or more selected from the group consisting of petroleum ether, toluene, chloroform, ethanol, and water.

8. The method for preparing the high-purity, thermostable crystal of the 2-[(2,4-dichlorophenyl)methyl]-4,4-dimethyl-3-isoxazolidinone compound (Formula I) according to claim 6, wherein the content of the 2-[(2,4-dichlorophenyl)methyl]-4,4-dimethyl-3-isoxazolidinone compound (Formula I) is greater than 99%.

9. An agrochemical formulation comprising the crystal of the 2-[(2,4-dichlorophenyl)methyl]-4,4-dimethyl-3-isoxazolidinone compound (Formula I) according to claim 1 for the control of unwanted weeds for protecting crops.

10. The agrochemical formulation according to claim 9, wherein the agrochemical formulations are a water dispersible granule or a suspension concentrate; wherein the crops comprise corn, wheat, rape, rice, sorghum, barley or rye; and wherein the weeds comprise Echinochloa crus-galli, Digitaria sanguinalis, Setaria viridis, Eleusine indica, Cynodon dactylon, Phragmites australis, Cyperus iria, Polygonum L., Xanthium sibiricum, abutilon, Portulaca oleracea, Solanum nigrum, Chenopodiaceae, Acalypha australis, Malachium aquaticum, Amaranthus retroflexus, Portulaca oleracea, Amaranthus blitum, Conyza Canadensis, Elsholtzia ciliata, Cirsium japonicum, Cirsium setosum, Sonchus oleraceus L., Eclipta prostrata, Calystegia hederacea, Parthenocissus tricuspidata, Commelina communis, Capparis spinosa L., Plantago asiatica, Medicago sativa L., Glycine soja, Alopecurus aequalis, Alopecurus japonicus, Beckmannia syzigachne Bromus japonicus Thunb, Poa annua, Avena fatua, Polypogon, Lolium perenne, Aegilops tauschii, Stellaria uliginosa, Galium spurium, Stellaria media, Cerastium arvense, Veronica didyma, Cardamine hirsuta, Polygonum lapathifolium, Vicia sativa, Capsella bursa-pastoris, Ixeris

*denticulata, Hemistepta lyrata, Oxalis corniculata, Euphorbia helioscopia, Convolvulus arvensis, Silene conoidea, Chenopodium serotinum* L., *Polygonum aviculare* L., *Rumex dentatus, Thlaspi arvense, Lapsana apogonoides, Lamium amplexicaule, Rotala indica, Abutilon theophrasti,* AstilberivularisBuch.-Ham. ex D. Don., *Ambrosia artemisiifolia, Leymus chinensis, Lolium multiflorum, Datura stramonium, Sorghum halepeme, Pharbitis* Choisy, *Elytrigia, Helianthus annuus, Polygonum convolvulus, Sinapis arvensis, Setaria glauca,* green foxtail, *Chenopodium album, Commelina benghalensis, Nigella damascena, Brachiara eruciformis, Cirsium arvense, Xanthium pensylvanicum, Papaver rhoeas, Matthiola incana, Setaria viridis* sp. *Pycnocoma,* hairy beggarticks, *Nigella damascena,* horseweed, largecrabgrass, littleseed canarygras, Pennsylvaniasmartweed, pitted morningglory, *Sida spinosa* L., *Apera spica-venti,* wild poinsettia and *Cyperus esculentus.*

11. The method for preparing the seed crystal of the crystal of the 2-[(2,4-dichlorophenyl)methyl]-4,4-dimethyl-3-isoxazolidinone compound (Formula I) according to claim 4, wherein the solvent A is a petroleum ether, wherein a boiling range of the petroleum ether is between 60° C. and 90° C.

12. The agrochemical formulation according to claim 10, wherein the agrochemical formulation is water dispersible granule, wherein the crops are corn, wheat; and wherein the weeds are *Stellaria media, Poa annua* L.

\* \* \* \* \*